United States Patent [19]

Faustman et al.

[11] Patent Number: 5,139,481
[45] Date of Patent: Aug. 18, 1992

[54] TREATMENT FOR TYPE II DIABETES

[75] Inventors: Denise Faustman, Weston; Joseph Avruch, Brookline, both of Mass.

[73] Assignee: The General Hospital Corporation, Boston, Mass.

[21] Appl. No.: 741,850

[22] Filed: Aug. 7, 1991

[51] Int. Cl.⁵ ............................................. A61M 31/00
[52] U.S. Cl. .......................................................... 604/49
[58] Field of Search ..................................... 604/27, 49

[56] References Cited

U.S. PATENT DOCUMENTS 4,542,143  9/1985  Hosokawa et al. ................. 514/356

Primary Examiner—Gene Mancene
Assistant Examiner—Michael Lynch
Attorney, Agent, or Firm—Fish & Richardson

[57] ABSTRACT

Disclosed is a method for treating insulin resistance in a patient which involves isolating a skeletal muscle cell from an insulin-sensitive donor and transplanting the skeletal muscle cell into the skeletal muscle tissue of the insulin-resistant patient. The transplanted cell may be a muscle precursor cell, e.g., a myoblast or it may be derived from whole skeletal muscle tissue.

12 Claims, No Drawings

TREATMENT FOR TYPE II DIABETES

BACKGROUND OF THE INVENTION

This invention relates to treatments for Type II diabetes.

Diabetes mellitus is characterized by hyperglycemia, the delayed onset of a highly specific set of microvascular abnormalities in the retina, kidney, and peripheral nerves, and an unusually high prevalence of atherosclerotic vascular disease, qualitatively similar to that seen in the nondiabetic population. The illness is common, affecting at least 2% of individuals of all ages in the U.S. Two broad clinical forms, i.e., Type I and Type II, encompass >98% of all cases.

Type I diabetes, previously called juvenile-onset or early-onset diabetes, accounts for 10–20% of all cases. The underlying cause of Type I diabetes appears to be an autoimmune destruction of the insulin-secreting $\beta$-cells of the pancreas.

The proximate cause of Type II diabetes, which accounts for 80–90% of all cases, is not yet known. It is known, however, that this illness is found in 1 out of 20 adults over the age of 40 and that it increases in prevalence with age. It is also known that the disease is characterized by two coexisting metabolic defects. First, nearly all patients with Type II diabetes exhibit a marked resistance to the hypoglycemic actions of insulin. In physiologic terms, uptake of glucose into skeletal muscle (i.e., the major site of insulin-mediated glucose conversion) is impaired at all plasma insulin concentrations; this is combined with a failure of low concentrations of insulin to suppress glucose production by the liver (see, e.g., DeFronzo, Diabetes 37:667, 1988). Such insulin resistance results in a situation where the patient, although producing detectable and often considerable amounts of endogenous insulin, is unable to overcome the impedence to insulin action. In certain instances, insulin resistance is further complicated by a coexisting deficiency in endogenous insulin secretion.

Such chronic hyperglycemia with or without insulin deficiency often results in unfavorable secondary consequences. For example, insulin action and insulin secretion may be further impaired by processes different, and additive to, those which initiated the insulin resistance and deficiency (Unger and Grunby, Diabetologia 28:119, 1985). In addition, chronic hyperglycemia is thought to cause renal, retinal, and neuropathic complications and to contribute substantially to accelerated atherosclerosis.

SUMMARY OF THE INVENTION

In general, the invention features a method of treating insulin resistance in a patient which involves isolating a skeletal muscle cell from an insulin-sensitive donor and transplanting the skeletal muscle cell into the insulin-resistant patient.

In various preferred embodiments, the skeletal muscle cell is a muscle precursor cell (preferably, a myoblast) or is derived from whole skeletal muscle tissue; the skeletal muscle cell is propagated in vitro prior to transplant; and the skeletal muscle cell is introduced into a skeletal muscle tissue of the patient. The skeletal muscle cell may be derived from an allogeneic, isogenic, or xenogeneic donor.

In other preferred embodiments, the insulin resistant patient has Type II diabetes, is hypertensive, or has hypertriglyceridemia.

By "insulin resistance" is meant an impaired ability to take up glucose and/or convert glucose to glycogen in vivo, e.g., in skeletal muscle.

By "insulin sensitive" is meant responsive to insulin action (including the uptake of glucose) at a clinically-normal level.

By "muscle precursor cell" is meant any cell which matures into a skeletal muscle cell. One such muscle precursor cell is a "myoblast", i.e., a committed, but as yet undifferentiated, muscle stem cell having proliferative potential.

By "whole skeletal muscle tissue" is meant a sample of skeletal muscle tissue which includes both mature (i.e., differentiated) and immature (i.e., less than fully differentiated) skeletal muscle cells.

By "hypertensive" is meant characterized by or suffering from abnormally increased blood pressure (e.g., blood pressure greater than 140 systolic and 90 diastolic).

The instant invention provides methods for the treatment of Type II diabetes which do not require the administration of daily doses of insulin or hypoglycemic agents which may themselves contribute to atherosclerotic vascular disease (e.g., by promoting hyperglyceridemia and/or hypertension). The methods also obviates strict diets or exercise regimens which patients generally find difficult to maintain. This is of particular advantage, e.g., to Type II diabetes patients for whom such an exercise regimen is physically impossible or impractical for medical reasons. Such patients include those suffering from peripheral or coronary atherosclerosis, peripheral neuropathy, retinopathy, or other age-related conditions (e.g., osteoporosis), all conditions which are common in Type II diabetes patients.

DETAILED DESCRIPTION

As discussed above, Type II diabetes is characterized by a marked resistance to insulin action (termed "insulin resistance"). The dominant site of insulin resistance appears to be skeletal muscle tissue (DeFronzo, supra), consistent with the dominant role of this tissue in the insulin-mediated uptake of glucose and conversion of glucose to glycogen (Lillioja et al., N. Eng. J. Med. 318:1217, 1988; Shulman et al., N. Eng. J. Med. 322:223, 1990).

Applicants have recognized that Type II diabetes may be treated by targeting a reversal of such skeletal muscle-mediated insulin resistance, i.e., by restoring a high peripheral responsiveness to insulin. Their method generally involves transplantation of skeletal muscle cells from an "insulin-responsive" (i.e., a non-Type II diabetic) donor into the insulin-resistant patient. The transplanted muscle tissue promotes efficient utilization of glucose, thereby reversing the patient's diabetic condition.

There now follow two examples of transplantation methods according to the invention. These examples are provided to illustrate, not limit, the invention.

TRANSPLANTATION OF SKELETAL MYOBLAST CELLS

In this method, skeletal muscle precursor cells (specifically, myoblast cells) are transplanted from an insulin-sensitive donor to the Type II diabetic (i.e., insulin-resistant) patient as follows.

Donors are chosen as follows. Humans, preferably young adults, with no family history of Type II diabetes, hypertension, or hyperlipidemia are pre-screened for evidence of transmissible infectious disease (e.g., HIV, CMV, hepatitis A/B). Potential donors who test negative for such infectious diseases are then screened for insulin responsiveness (i.e., insulin sensitivity). Insulin responsiveness is assayed by an intravenous glucose tolerance test (e.g., as described in Bergmann, Diabetes 1512, 1989) or by a hyperinsulemic, euglycemic clamp study as described in Andres et al. in DeFronzo et al. (Am. J. of Physiol. 273:E214, 1979). In addition, fasting and postglucose ingestion levels of plasma glucose and insulin are measured, as well as blood pressure and fasting triglycerides. Individuals exhibiting low fasting plasma insulin levels, high glucose tolerance levels, and high levels of insulin-stimulated glucose utilization (i.e., high M values) are selected as donors. To reduce the severity of immune rejection, histocompatibility typing is also performed. Class I and class II histocompatibility antigens are determined and individuals closely matched immunologically to the patient are selected as donors. Donors of skeletal muscle may be living or, alternatively, muscle explants may be obtained postmortem.

A skeletal muscle explant is then obtained from the donor. Such a skeletal muscle biopsy is a structural and functional syncytium including "rests" of skeletal muscle precursor cells, termed myoblasts or satellite cells (Lipton et al., Science 205:1292, 1979; Partridge et al, Nature 73:306, 1978). Such myoblasts initially proliferate in vivo (and in vitro) as single cells (Bischoff, Dev. Biol 115:129, 1986). As they approach their mature state, multiple myoblast cells fuse into a single, multinucleated cell, termed a myotube, whose cytoplasmic content reflects the contribution of each of the individual precursor cells (Frair et al., Exp. Cell. Res. 145:167, 1983; Pavlath et al., Nature 337:570, 1989).

In one specific method, a skeletal muscle fragment up to 3 g in size is excised from a major muscle group (e.g., Vastus lateralis). Muscle is separated from adjacent fat or contaminating fibrous tissue, minced finely with curved scissors, and divided into several test tubes containing calcium and magnesium-free Hanks medium (pH 7.4); each test tube contains between 0.5 mg and 5 mg of muscle tissue. Tissue is digested with trypsin and (when necessary) 0.6–10% collagenase. Following digestion for 7 min at 37° C., the muscle suspension is aspirated in and out of a Pasteur pipette for an additional 7-15 min. Large muscle fragments are then allowed to settle, the supernatant is removed, and excess medium is added to the precipitate to stop the digestion reaction. Digestion of any remaining muscle fragments is repeated until a suspension of single cells suitable for tissue culturing is obtained. Cells are washed to remove proteases and are stored at 4° C.

Myoblasts are isolated and induced to proliferate in vitro generally as described in Bischoff (supra). Muscle cultures are plated at a concentration of $3 \times 10^6$ viable cells/ml and maintained at subconfluency (i.e., a maximum of approximately $2 \times 10^6$ cells/ml) to prevent myotube fusion leading to loss of myoblasts. Following centrifugation (at 200 g for 10 min) and resuspension in growth medium (e.g., Medium 199 containing Earle's salts, HEPES buffer, glutamine, 10% fetal calf serum, 2% chick embryo extract, and penicillin; GIBCO, Grand Island, N.Y.), cell yield is estimated by counting a known volume of cell suspension in a hemocytometer. Cell viability is determined by trypan blue exclusion.

Myogenic cells are isolated following an initial cell expansion of 3-5 doublings. Myoblasts are purified by luorescent-activated cell sorting (by the instructions of the manufacturer, Coulter Immunology, Hialeah, Fla.) using monoclonal antibody 5.10 H11 (specific for NCAM, a human myoblast-specific cell surface antigen). Such a monoclonal antibody is available, e.g., from Seratec Ltd. (Oxford, England). Once harvested, myoblasts are stored frozen (at −35° C.) and remain viable for years.

Myoblasts are chosen which have a high capacity for cell fusion and concomitant differentiation into myotubes. This characteristic is assayed by allowing a sample of cultured myoblasts to fuse into myotubes, e.g., by allowing the cells to reach confluence (or to otherwise induce cell-cell contact) or by inducing myotube differentiation by growing cells in medium with reduced serum (e.g., RPMI medium containing 0.5% serum; GIBCO) for 1-2 days. To assay the efficiency of cell fusion, cells are fixed for 6 min. in methanol, stained for 20 minutes with 10% Giemsa solution, rinsed 3 times with 5-6 ml of water, and scored for cell fusion using light microscopy at a magnification of 250X. The total number of nuclei, the total number of nuclei in myotubes, and the total number of myotubes are counted; cells containing three or more nuclei are scored as myotubes. The fusion percentage is calculated as the ratio of nuclei included in myotubes to the total number of nuclei (i.e., in both myoblasts and myotubes).

The responsiveness of donor myotubes to insulin (i.e., ability to take up glucose and convert it to glycogen) is also assayed in vitro. Following conversion to myotubes (by the standard conditions described above), insulin dose-response (i.e., for conversion of glucose to glycogen and concomitant activation of glycogen synthase) is measured by the method of Witters and Avruch, J. Biochem. 17:406, 1978). The efficacy of a particular myotube sample is compared with other myotube samples of similar muscle fiber type (e.g., red versus white, Type I versus Type II) since fibers of different phenotype exhibit different insulin sensitivity in vivo (James et al, Amer. J. Physiol. 248:E567, 1985). Myoblasts are chosen which give rise to myotubes exhibiting normal or high insulin responsiveness (i.e., ability to restore insulin sensitivity).

Approximately $10^4$ myoblasts are generally isolated from a 100-mg fragment of adult human skeletal muscle (Webster et al., Exp. Cell. Res. 174:252. 1988). Because each myoblast has the potential for 30-40 doublings in vivo (without significant loss of myogenicity or fusion capacity) (Webster et al., supra), a 1-gm muscle biopsy yields $10^{14}$–$10^{17}$ myoblasts. In animal model studies (see, Morgan et al., J. Neural. Sci. 86:137, 1988; Partridge et al., Nature 337:176, 1989), implantation of $10^6$ myoblasts/100 mg muscle was required for partial correction of muscle enzyme defects. Extrapolating to humans, a 70 kg human has approximately 40 kg of skeletal muscle. Thus, $4 \times 10^{12}$ myoblasts should be sufficient to restore insulin sensitivity; this number of myoblasts is generally produced from a single 100 mg skeletal muscle biopsy.

To transplant the myoblast cells into a human recipient a preparation of mononucleated muscle cells is suspended in sterile growth medium (e.g., RPMI with 10% serum) at a concentration of $10^8$ to $10^9$ cells/ml and injected at multiple sites into any large skeletal muscle, e.g. Gluteus maximus or Vastus lateralis. Approximately $10^{10}$ total myoblasts are administered at each of multiple injection sites; injection sites are generally spaced approximately one centimeter apart. Prior to implantation, it may be desirable to prepare the patient with needle-induced trauma of the muscle site to initiate proliferation of endogenous myoblasts and to promote maximal cell fusion.

Therapeutic response is gauged by changes in fasting insulin and glucose tolerance (as described above) measured 4-6 weeks post-injection. Subsequent injections are performed as necessary (as indicated by metabolic testing, described above); they are repeated, e.g., at 30 day intervals over a period of 12-40 months.

To optimize the likelihood of successful transplant, the closest possible immunological match between donor and recipient is desired. To accomplish this, donor and recipient Class I and Class II histocompatibility antigens are determined and donor skeletal muscle of greatest similarity utilized. This minimizes or eliminates immune rejection and reduces the need for immunosuppressive or immunomodulatory therapy. Expression of MHC antigens on mature human skeletal muscle is very low; this likely facilitates graft acceptance (Karpati et al., Ann. Neurol. 23:64, 1988).

Immunosuppressive or immunomodulatory therapy, when required, consists of a limited period of cyclosporin A treatment just prior to and during transplant. Cyclosporin A treatment apparently does not prevent or impair myoblast fusion; in previous studies, transiently-administered immunosuppressive therapy of this sort allowed allografted mononuculeated myoblast cells to incorporate into host muscle fibers (see, e.g., Watt et al., Clin. Exp. Immunol. 55:419, 1988).

Immunological tolerance may also be induced prior to transplant by the method of Watt et al. (supra), allowing untreated allogeneic myoblasts to fuse and to survive without concomitant immunosuppressive treatment of the recipient. Alternatively, allogeneic or xenogeneic tissue may be masked prior to transplantation by the method of Faustman and Coe (Science 252:1701, 1991); rejection is prevented because the recipient's lymphocytes do not efficently adhere to the foreign myoblast cells.

TRANSPLANTATION OF WHOLE SKELETAL MUSCLE TISSUE

Insulin responsiveness may also be restored to an insulin-resistant patient by a whole muscle transplant from an insulin-sensitive donor as follows.

Donors are chosen as described above. Again a preferable donor has no family history of Type II diabetes, is insulin-responsive, and is closely matched to the recipient immunologically. Whole skeletal muscle is first excised from a major muscle group. The muscle is separated (e.g., by blunt dissection) from adjacent fat or contaminating fiber tissue and stored (for up to 24 hours) in serum-free Hanks medium or transplant preservative solution.

The skeletal muscle transplant may be introduced either subcutaneously or intraperitonally by standard surgical techniques. Between 0.1 kg and 30 kg of muscle tissue are transplanted in a single session. Subsequent transplants may be repeated as necessary (as indicated by metabolic testing, described above). If necessary, immunosuppressive or immunomodulatory therapy is carried out also as described above. Such therapy may include treatment with cyclosporin A or aziothioprine and steroids and/or it may involve the immunosuppressive techniques of Watt et al., supra, or Faustman and Coe, supra).

We claim:

1. A method of treating insulin resistance in a patient, comprising isolating a skeletal muscle cell from an insulin-sensitive donor and transplanting said skeletal muscle cell into said insulin-resistant patient.

2. The method of claim 1, wherein said skeletal muscle cell is a muscle precursor cell.

3. The method of claim 2, wherein said muscle precursor cell is a myoblast.

4. The method of claim 2, wherein the isolated muscle cell is propagated in vitro prior to transplant.

5. The method of claim 2, wherein said transplanted cell is introduced into a skeletal muscle tissue of said patient.

6. The method of claim 1, wherein said skeletal muscle cell is derived from whole skeletal muscle tissue.

7. The method of claim 1, wherein said skeletal muscle cell is derived from an allogeneic donor.

8. The method of claim 1, wherein said skeletal muscle cell is derived from an isogenic donor.

9. The method of claim 1, wherein said skeletal muscle cell is derived from a xenogeneic donor.

10. The method of claim 1, wherein said patient has Type II diabetes.

11. The method of claim 1, wherein said patient is hypertensive.

12. The method of claim 1, wherein said patient has hypertriglyceridemia.

* * * * *

UNITED STATES PATENT AND TRADEMARK OFFICE
CERTIFICATE OF CORRECTION

PATENT NO. : 5,139,481

DATED : August 18, 1992

INVENTOR(S) : Denise Faustman and Joseph Avruch

It is certified that error appears in the above-indentified patent and that said Letters Patent is hereby corrected as shown below:

On the title page, item [56], under "OTHER PUBLICATIONS", add the following:

Saad, "A Two-Step Model for Development of Non-Insulin-Dependent Diabetes", The American Journal of Medicine, Vol. 90, pp. 229-235 (February 1991);

Dent et al., "The Molecular Mechanism by Which Insulin Stimulates Glyogen Synthesis in Mammalian Skeletal Muscle", Nature, Vol. 348, pp. 302-308 (November 22, 1990);

Shulman et al., "Quantitation of Muscle Glycogen Synthesis in Diabetes, The New England Journal of Medicine, Vol. 322, No. 4, pp. 223-228 (January 25, 1990);

Partridge et al., "Conversion of MDX Myofibres from Dystrophin-Negative to -Positive by Injection of Normal Myoblasts", Nature, Vol. 337, pp. 176-179, January 12, 1989;

Reaven, "Banting Lecutre 1988 - Role of Insulin Resistance in Human Disease", Diabetes, Vol. 37, pp. 1595-1607, December, 1988;

DeFronzo, "Lilly Lecture 1987 - The Triumvirate: $\beta$-Cell, Muscle, Liver- A Collusion Responsible for NIDDM", Diabetes, Vol. 37, pp. 667-687, June, 1988;

UNITED STATES PATENT AND TRADEMARK OFFICE
CERTIFICATE OF CORRECTION

PATENT NO. : 5,139,481

DATED : August 18, 1992

INVENTOR(S) : Denise Faustman and Joseph Avruch

It is certified that error appears in the above-identified patent and that said Letters Patent is hereby corrected as shown below:

Lillioja et al., "Impaired Glucose Tolerance as a Disorder of Insulin Action", The New England Journal of Medicine, Vol. 318, No. 19, pp. 1217-1225, May 12, 1988;

Webster et al., "Isolation of Human Myoblasts with the Fluorescence-Activated Cell Sorter", Experimental Cell Research, Vol. 174, pp. 252-265, (1988);

Morgan et al., "Partial Correction of an Inherited Biochemical Defect of Skeletal Muscle of Grafts of Normal Muscle Precursor Cells", Journal of the Neurological Sciences, Vol. 86, pp. 137-147, (1988);

Bischoff, "Proliferation of Muscle Satellite Cells on Intact Myofibers in Culture", Developmental Biology, Vol. 115, pp. 129-147, (1986);

Bogardus et al., "Correlation Between Muscle Glycogen Synthase Activity and In Vivo Insulin Action in Man", The Journal of Clinical Investigation, Inc., Vol. 73, pp. 1185-1190, April 1984;

Frair et al., "The Nuclear-Cytoplasmic Relationship in 'Mosaic' Skeletal Muscle Fibers from Mouse Chimaeras", Experimental Cell Research, Vol. 145, pp. 167-178, (1983);

UNITED STATES PATENT AND TRADEMARK OFFICE
CERTIFICATE OF CORRECTION

PATENT NO.   : 5,139,481

DATED        : August 18, 1992

INVENTOR(S)  : Denise Faustman and Joseph Avruch

It is certified that error appears in the above-identified patent and that said Letters Patent is hereby corrected as shown below:

Olefsky et al., "Insulin Action and Resistance in Obesity and Noninsulin-Dependent Type II Diabetes Mellitus", The American Physiological Society, pp. E15-E30 (1982);

Lipton et al., "Developmental Fate of Skeletal Muscle Satellite Cells, Science, Vol. 205, pp. 1292-1294, September 21, 1979;

Partridge et al., "Evidence of Fusion Between Host and Donor Myoblasts in Skeletal Muscle Grafts", Nature, Vol. 273, pp. 306-308, May 25, 1978;

Col. 3, line 31, change "Nature 73:306" to --Nature 273:306--;

Col. 4, line 5, correct the spelling of "fluorescent".

Signed and Sealed this

Twelfth Day of October, 1993

Attest:

BRUCE LEHMAN

*Attesting Officer*            *Commissioner of Patents and Trademarks*